United States Patent [19]

Lentz et al.

[11] Patent Number: 4,506,092
[45] Date of Patent: Mar. 19, 1985

[54] CARBONYLATION PROCESS FOR THE PRODUCTION OF AROMATIC ACIDS AND DERIVATIVES THEREOF

[75] Inventors: Carl M. Lentz, Mt. Carmel; James R. Overton; David D. Cornell, both of Kingsport, all of Tenn.

[73] Assignee: Eastman Kodak Company, Rochester, N.Y.

[21] Appl. No.: 628,352

[22] Filed: Jul. 6, 1984

[51] Int. Cl.$^3$ .............................................. C07C 69/76
[52] U.S. Cl. .................................. 560/103; 560/100; 560/105; 562/406; 564/180; 564/183; 564/166; 568/38; 546/298; 549/71; 549/72; 549/505; 549/506
[58] Field of Search ................ 560/103, 100, 105; 562/406; 564/180, 183, 166; 568/38; 546/298; 549/71, 72, 505, 506

[56] References Cited

U.S. PATENT DOCUMENTS

| | | | |
|---|---|---|---|
| 3,700,729 | 10/1971 | Fenlon | 562/406 |
| 3,709,326 | 10/1973 | Paulik et al. | 562/406 |
| 3,887,595 | 6/1975 | Nozaki | 562/406 |
| 3,965,132 | 6/1976 | Novell | 562/406 |

FOREIGN PATENT DOCUMENTS 82633  10/1983  European Pat. Off. ............ 562/406

*Primary Examiner*—Paul J. Killos
*Attorney, Agent, or Firm*—Clyde L. Tootle; David E. Cotey; J. Frederick Thomsen

[57] ABSTRACT

The present invention provides a process for the preparation of aryl carboxylic acids and derivatives thereof by the carbonylation of triaryl sulfonium salts. The triaryl sulfonium salts are reacted with carbon monoxide and water or an alcohol or amine in the presence of a triaryl phosphine and a zero-valent metal catalyst selected from palladium or rhodium.

15 Claims, No Drawings

CARBONYLATION PROCESS FOR THE PRODUCTION OF AROMATIC ACIDS AND DERIVATIVES THEREOF

DESCRIPTION

The present invention provides a novel catalytic carbonylation process for the production of aromatic acids, esters, and/or amides. The novel process involves the carbonylation of an aryl sulfonyl chloride in the presence of water, an alcohol, or an amine and a specified transition metal catalyst.

The preparation of carboxylic acid esters from organic halides by a carbonylation process has been described in U.S. Pat. No. 3,988,358. ("the Heck process"). In the disclosed process, carboxylic acid esters or amides are obtained from aryl halides and substituted derivatives thereof by the reaction of the chosen starting material with an alcohol or primary or secondary amine and carbon monoxide in the presence of a palladium catalyst. A typical example is the conversion of bromobenzene to n-butyl benzoate at 100° C. and one atmosphere of carbon monoxide in the presence of tri-n-butyl amine and a catalytic amount of $PdBr_2[P(C_6H_5)_3]_2$. This reaction does not involve the use of an aryl sulfonyl chloride as the starting material.

It also is known that diaryliodonium salts can be carbonylated to aromatic esters and amides in the presence of a metal catalyst. Specific metals which have been employed include palladium, rhodium, ruthenium, and molybdenum. See, for example, Nippon Kagaku Kaishi, 1982, No. 2, pp. 236–241, and co-pending U.S. patent application Ser. No. 628,352, filed July 6, 1984. Again, the carbonylation of an aryl sulfonyl chloride is not disclosed.

In contrast to the above-described processes, it has now been found that aryl sulfonyl chlorides can be carbonylated to desired aromatic acids or derivatives thereof in the presence of a specified catalytic species. This process thus provides a new and unique method for the replacement of a sulfur moiety with carbon. This transformation has practical applications in the preparation of polyesters and photographic intermediates.

SUMMARY OF THE INVENTION

The present invention provides a process for the preparation of compounds of the formula

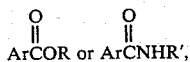

wherein R represents H or an aliphatic moiety having up to about 12 carbon atoms and wherein R' represents an aliphatic moiety having up to about 12 carbon atoms. The process comprises reacting a triaryl sulfonium salt of the formula

wherein Ar represents a carbocyclic or heterocyclic aromatic moiety having about 5 to about 20 atoms in the ring or rings thereof and X represents a weak acid anion, with (i) carbon monoxide and (ii) water or an aliphatic alcohol or primary amine having up to about 12 carbon atoms in the presence of a catalyst system comprising (i) a zero-valent metal catalyst selected from the group consisting of palladium, rhodium, and mixtures thereof, and (ii) a triaryl phosphine.

DETAILED DESCRIPTION OF THE INVENTION

The present invention relates to the production of aromatic carboxylic acids, esters, and/or amides by a process which involves the carbonylation of a triaryl sulfonium salt in the presence of a specified catalyst system.

The triaryl sulfonium salt employed as a starting material in the process of the present invention has the following chemical formula:

In the above formula, Ar represents a carbocyclic or heterocyclic aromatic moiety having about 5 to about 20 atoms in the ring or rings thereof. Such moieties can be derived from, for example, toluene, benzene, naphthalene, pyridine, thiophene, pyrrole, etc.

The aromatic moiety of the aryl sulfonyl chloride can be substituted or unsubstituted. When substituted, typical substituents include the halides, alkyl groups having up to about 12 carbon atoms, vinyl, carboxylic acid moieties, carboxylic ester moieties, ether groups, nitro groups, etc.

In the above formula, X represents a weak acid anion. Preferred examples of such anions include acetate, trihaloacetate (e.g., triiodoacetate), p-toluenesulfonate, benzenesulfonate, hydroxide, iodide, bromide, boron tetrafluoride, etc.

Thus, examples of suitable triaryl sulfonium salts include triphenyl sulfonium iodide, tritolyl sulfonium iodide, tritolyl sulfonium acetate, triphenyl sulfonium hydroxide, etc.

The triaryl sulfonium salts can be prepared by known methods. An electrochemical preparation of triaryl sulfonium salts is described in *Electrochemica Acta*, 28, 1465 (1983). The preparation of triaryl sulfonium salts from diaryliodonium salts is disclosed by Crivello et al. in *J. Org. Chem.*, 43, 3055 (1978). Wiegand et al. describe the preparation of triaryl sulfonium salts from sulfoxides in *J. Org. Chem.*, 33, 2671 (1968). Each of the disclosures listed above is hereby incorporated herein by reference in its entirety.

In accordance with the process of the present invention, an aryl sulfonyl chloride, as described above, is reacted with water or an aliphatic alcohol or primary amine having up to about 12 carbon atoms. In the case where water is employed as a reactant, an aromatic carboxylic acid is produced; when an alcohol is employed, the corresponding aromatic ester is produced; and when an amine is employed, the corresponding amide is produced.

In especially preferred embodiments of the present invention, aromatic esters are produced by the reaction of an aryl sulfonyl chloride with an alcohol as described above. The aliphatic alcohol which is employed in the present process may be monofunctional or multifunctional. Thus, glycols and other polyols are suitable, as are glycol esters, glycol ethers, and other such derivatives. Preferably, the alcohol comprises a lower alkanol (i.e., an alkanol having up to about 12 carbon atoms), ethylene glycol, propylene glycol, neopentyl glycol, ethylene glycol monoacetate, mixtures thereof, etc.

Suitable primary amines which may be employed in the preparation of amides by the process of the present invention include both aliphatic amines and aromatic amines. Suitable primary aliphatic amines include those having up to about 12 carbon atoms, such as monoethylamine, mono-n-butylamine, mono-2-ethylhexylamine, octylamine, dodecylamine, etc. Suitable aromatic amines include aniline, substituted anilines, etc. Multifunctional primary amines, such as the phenylenediamines, also may be used in the present process.

The reaction system of the present process further comprises a zero-valent metal catalyst. The catalyst is selected from the group consisting of palladium, rhodium, and mixtures thereof. Palladium is preferred for use as the zero-valent metal catalyst.

The active metal species is the zero-valent form of the metal. Therefore, in preferred embodiments, the catalyst is provided to the reaction system in the zero-valent form of the metal. More preferably, the zero-valent metal is supported on a suitable material. For example, a highly desirable catalyst material comprises 5% palladium on a carbon support. Of course, other zero-valent catalyst forms can be employed.

The catalyst metal may also be provided in a higher valence state, provided that an in situ reduction to the zero-valent form occurs. Thus, palladium salts, such as palladium acetate, palladium chloride, etc., are also suitable catalyst materials.

The metal catalyst is present in a concentration of at least about 0.01 millimole per mole of aryl sulfonyl chloride (preferably, about 0.1 to 1 millimole per mole).

The catalyst system of the present invention further comprises a triaryl phosphine. The triaryl phosphine is employed in a concentration of about 0.1 to 10 moles per mole of metal catalyst (preferably about 1 mole per mole of metal catalyst). Preferred triaryl phosphines include triphenyl phosphine, tritolyl phosphine, and mixtures thereof.

The catalytic carbonylation reaction of the present invention is conducted in the presence of carbon monoxide, which is employed in amounts such that the total reaction pressure is in the range of atmospheric to about 500 psig. Superatmospheric pressure may be advantageous when a volatile reactant is employed or when an increase in the rate of reaction is desirable. Thus, reaction pressures from atmospheric pressure up to about 500 psig (about 3500 kPa) are suitable, with pressures from atmospheric pressure up to about 100 psig (about 800 kPa) being preferred.

The process of the present invention can be conducted at room temperature or at elevated temperatures up to about 150° C. Preferably, the temperature of the reaction is in the range of about 25° to 75° C.

It may be desirable also to include in the reaction system a base having a $pK_a$ greater than that of pyridine. The presence of such a base may aid in the prevention of deactivation of the metal catalyst. When employed, the base is present in an amount of about 1 to 10 equivalents of base per equivalent of sulfonyl chloride. Preferably, about 3 equivalents of base per equivalent of sulfonyl chloride is employed. Preferred bases include trialkylamines (such as triethylamine), sodium carbonate, potassium carbonate, etc.

Inert coordinating solvents may be employed, but are not necessary. Such solvents may include, for example, tetrahydrofuran, acetonitrile, etc. In those aspects of the present invention wherein aromatic esters are produced by the reaction of an aryl sulfonyl chloride with carbon monoxide and an alcohol, the alcohol can be employed as solvent. Likewise, when preparing amides, the amine can be employed as solvent.

While not wishing to be bound by theoretical considerations, it is believed that the process of the present invention involves the following reaction pathway:

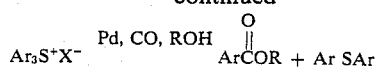

The diarylsulfide by-product can be separated from the ester and converted by known methods to starting material as shown below:

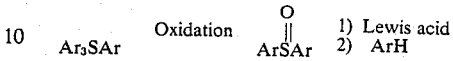

The process of the present invention represents a unique catalytic carbonylation process for the conversion of aromatic compounds to corresponding acids and derivatives thereof. The products of the present process are useful as intermediates in the manufacture of photographic chemicals and in the synthesis of polyesters (such as polyethylene terephthalate) and other useful polymeric materials.

The invention will be further illustrated by the following Examples although it will be understood that these Examples are included merely for purposes of illustration and are not intended to limit the scope of the invention.

EXAMPLE 1

A 100 ml, three-neck, round-bottom flask was fitted with a reflux condenser, a thermometer, a magnetic stirrer, and a gas inlet tube. To the above-described apparatus were added 1.0 g (2.3 millimoles) of tritolyl sulfonium iodide, 0.1 g (0.45 millimoles) of palladium acetate, 1.0 g sodium carbonate, and 50 ml of methanol. The resulting mixture was heated to reflux (60° C) while carbon monoxide was fed beneath the surface of the mixture. The reaction mixture was maintained at reflux for two hours while carbon monoxide was continually fed to the reaction system. At the completion of the reaction time period, the reaction mixture was cooled and filtered through a Celite pad, and water (200 ml) was added to the reaction mixture. The aqueous phase was extracted two times with 50 ml of diethyl ether. The extracts were combined, washed with 100 ml of water, and dried over magnesium sulfate. The ether was removed *in vacuo* to afford 0.50 g of a light-colored oil. GLPC analysis as compared to authentic samples indicated a conversion of 27% (82% yield) to methyl p-toluate. The product mixture contained 70% ditolylsulfide and 2% toluene.

EXAMPLE 2

Example 1 was repeated except that $Rh_2(OAc)_4$ was employed in place of palladium acetate. The yield of methyl p-toluate approached 100%. However, relatively large amounts of by-products (8.7% iodotoluene and 4.1% toluene) were present in the product mixture, and the ditolylsulfide by-product could not be accounted for accurately.

EXAMPLE 3

Example 1 was repeated except that triethylamine was employed in place of sodium carbonate. Methyl p-toluate was obtained in a yield of 24%. Thus, this example demonstrates that the less basic triethylamine is less favorable than the more basic inorganic carbonates in the process of the present invention:

COMPARATIVE EXAMPLE 1

Example 1 was repeated except that palladium acetate was omitted from the reaction system. No evidence of reaction was observed. Thus, this comparative example demonstrates the necessity of the inclusion of a specified zero-valent metal catalyst (i.e., rhodium or palladium) in the process of the present invention.

EXAMPLE 4

Example 1 was repeated except that sodium methoxide was employed in place of sodium carbonate. Methyl p-toluate was obtained in a yield of 79% (26% conversion), and the product mixture contained 6% toluene, 3% iodotoluene, and 61% ditolylsulfide.

EXAMPLE 5

Example 1 was repeated except that the triarylsulfonium salt was tritolyl sulfonium methoxide and no additional base was provided to the reaction system. The methoxy anion of the starting material proved to provide sufficient basicity to the reaction system to stabilize the metal catalyst. Methyl p-toluate was obtained in a yield of 76% (26% conversion), and the product mixture contained 6% toluene, 2% methoxytoluene, and 60% ditolylsulfide.

EXAMPLE 6

Example 1 was repeated except that potassium carbonate was employed in place of sodium carbonate. Methyl p-toluate was obtained in a yield of 79% (26% conversion). The product mixture contained 4% toluene, 68% ditolylsulfide, and no detectable quantities of iodotoluene.

EXAMPLE 7

Example 6 was repeated except that the sulfonium salt was tritolyl sulfonium bromide. Methyl p-toluate was obtained in a yield of 82% (27% conversion). The product mixture contained 5% toluene, 65% ditolylsulfide, and no detectable quantities of bromotoluene.

EXAMPLE 8

Example 6 was repeated except that the sulfonium salt was tritolyl sulfonium chloride. Methyl p-toluate was obtained in a yield of 64% (21% conversion). The product mixture contained 2% chlorotoluene, 4% toluene, and 72% ditolylsulfide.

EXAMPLE 9

Example 6 was repeated except that the sulfonium salt was triphenyl sulfonium iodide. Methyl benzoate was obtained in a yield of 85% (28% conversion). The product mixture contained 4% benezene and 68% diphenyl sulfide.

EXAMPLE 10

Example 6 was repeated except that the sulfonium salt was tri(methoxyphenyl)sulfonium iodide. Methyl benzoate was obtained in a yield approaching 100%. The product mixture contained 3% benzene and 61% diphenyl sulfide.

The invention has been described in detail with particular reference to preferred embodiments thereof, but it will be understood that variations and modification can be effected within the spirit and scope of the invention.

We claim:

1. A process for the preparation of compounds of the formula

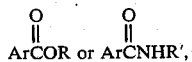

ArCOR or ArCNHR', wherein R represents H or an aliphatic moiety having up to about 12 carbon atoms and R' represents an aliphatic moiety having up to about 12 carbon atoms, said process comprising reacting an aryl sulfonyl chloride of the formula

$Ar_3S^+X^-$, wherein Ar represents a carbocyclic or heterocyclic aromatic moiety having about 5 to about 20 atoms in the ring or rings thereof, and X represents a weak acid anion, with (i) carbon monoxide and (ii) water or an aliphatic alcohol or primary amine having up to about 12 carbon atoms in the presence of a catalyst system comprising (i) a zero-valent metal catalyst selected from the group consisting of palladium, rhodium, and mixtures thereof, and (ii) a triaryl phosphine.

4. The process of claim 1 wherein $X^-$ represents acetate, trihaloacetate, p-toluenesulfonate, benzenesulfonate, hydroxide, iodide, bromide, or boron tetrafluoride.

5. The process of claim 1 wherein said metal catalyst comprises palladium.

6. The process of claim 1 wherein said triaryl phosphine comprises triphenyl phosphine, tritolyl phosphine, or a mixture thereof.

7. The process of claim 1 wherein the reaction temperature is about 25 to 150° C.

8. The process of claim 1 wherein the reaction system further comprises a base having a $pk_a$ greater than that of pyridine.

9. The process of claim 8 wherein said base comprises triethylamine, sodium carbonate, potassium carbonate, or an alkali alkoxide.

10. The process for the preparation of aromatic esters which comprises reacting at a temperature of about 25 to 150° C a triarylsulfonium salt of the formula

$Ar_3S^+X^-$, wherein Ar represents a moiety derived from toluene, benzene, naphthalene, pyridine, thiophene, or pyrrole, and X represents a weak acid anion comprising acetate, trihaloacetate, p-toluenesulfonate, benzenesulfonate, hydroxide, iodide, bromide, or boron tetrafluoride, with carbon monoxide and an alcohol comprising a lower alkanol, ethylene, glycol, propylene glycol, neopentyl glycol, ethylene glycol monoacetate, or a mixture thereof in the presence of a zero-valent palladium catalyst, a triaryl phosphine, and a base having a $pK_a$ greater than that of pyridine.

11. The process of claim 10 wherein Ar represents a moiety derived from toluene or benzene.

12. The process of claim 10 wherein said alcohol comprises methanol, ethylene glycol, ethylene glycol monoacetate, or a mixture thereof.

13. The process of claim 10 wherein said triaryl phosphine comprises triphenyl phosphine, tritolyl phosphine, or a mixture thereof.

14. The process of claim 10 wherein the reaction temperature is about 25° to 75° C.

15. The process of claim 10 wherein said base comprises triethylamine, sodium carbonate, potassium carbonate, or an alkali alkoxide.

* * * * *